United States Patent
Aghassian et al.

(10) Patent No.: US 9,833,627 B2
(45) Date of Patent: Dec. 5, 2017

(54) EXTERNAL TRIAL STIMULATOR USEABLE IN AN IMPLANTABLE NEUROSTIMULATOR SYSTEM

(71) Applicant: Boston Scientific Neuromodulation Corporation, Valencia, CA (US)

(72) Inventors: Daniel Aghassian, Glendale, CA (US); Robert G. Lamont, Van Nuys, CA (US); Robert J. Stinauer, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/991,582

(22) Filed: Jan. 8, 2016

(65) Prior Publication Data

US 2016/0114178 A1 Apr. 28, 2016

Related U.S. Application Data

(62) Division of application No. 13/287,775, filed on Nov. 2, 2011, now Pat. No. 9,259,574.

(60) Provisional application No. 61/414,630, filed on Nov. 17, 2010.

(51) Int. Cl.

| | |
|---|---|
| *A61N 1/378* | (2006.01) |
| *A61N 1/372* | (2006.01) |
| *A61N 1/02* | (2006.01) |
| *A61N 1/36* | (2006.01) |
| *A61N 1/375* | (2006.01) |

(52) U.S. Cl.
CPC ......... *A61N 1/37241* (2013.01); *A61N 1/025* (2013.01); *A61N 1/36017* (2013.01); *A61N 1/375* (2013.01); *A61N 1/3787* (2013.01); *Y10T 29/49002* (2015.01)

(58) Field of Classification Search
CPC ...................................................... A61N 1/025
See application file for complete search history.

(56) References Cited

U.S. PATENT DOCUMENTS

| | | | |
|---|---|---|---|
| 5,637,417 | A | 6/1997 | Engmark et al. |
| 6,263,245 | B1 | 7/2001 | Snell |
| 6,516,227 | B1 | 2/2003 | Meadows et al. |
| 6,687,538 | B1 | 2/2004 | Hrdlicka et al. |
| 7,359,751 | B1 | 4/2008 | Erickson et al. |

(Continued)

OTHER PUBLICATIONS

U.S. Appl. No. 61/406,341, filed Oct. 25, 2010, Aghassian, et al.

(Continued)

*Primary Examiner* — Carl H Layno
*Assistant Examiner* — Jennifer Ghand
(74) *Attorney, Agent, or Firm* — Lewis, Reese & Nesmith, PLLC

(57) ABSTRACT

An improved external trial stimulator provides neurostimulation functionality for implanted medical electrodes prior to implantation of an implantable neurostimulator. The external trial stimulator is housed in a four-part housing that provides mechanical and electrostatic discharge protection for the electronics mounted in a central frame of the housing. Connectors attached to leads from the electrodes connect to contacts that are recessed in the housing through ports that are centered for easy access. Multiple indicators provide information to users of the external trial stimulator.

18 Claims, 10 Drawing Sheets

(56) References Cited

U.S. PATENT DOCUMENTS

| | | |
|---|---|---|
| 7,899,529 B2 | 3/2011 | Powers |
| 2003/0139782 A1 | 7/2003 | Duncan et al. |
| 2004/0115990 A1* | 6/2004 | Kodama ............ H01R 13/6271 |
| | | 439/607.24 |
| 2004/0171914 A1* | 9/2004 | Avni ...................... A61B 1/041 |
| | | 600/160 |
| 2006/0099837 A1 | 5/2006 | Cheng et al. |
| 2006/0265020 A1 | 11/2006 | Fischell et al. |
| 2007/0027501 A1 | 2/2007 | Jensen et al. |
| 2007/0055318 A1 | 3/2007 | Forsberg et al. |
| 2010/0106206 A1 | 4/2010 | Aghassian et al. |
| 2010/0228324 A1 | 9/2010 | Lamont et al. |
| 2012/0101551 A1 | 4/2012 | Aghassian et al. |

OTHER PUBLICATIONS

International Search Report and Written Opinion regarding corresponding PCT Application No. PCT/US2011/058965, dated Jan. 5, 2012.

\* cited by examiner

EXTERNAL TRIAL STIMULATOR USEABLE IN AN IMPLANTABLE NEUROSTIMULATOR SYSTEM

CROSS REFERENCE TO RELATED APPLICATIONS

This is a divisional application of U.S. patent application Ser. No. 13/287,775, now U.S. Pat. No. 9,259,574, filed Nov. 2, 2011, which in turn is a non-provisional application of U.S. Provisional Patent Application Ser. No. 61/414,630, filed Nov. 17, 2010. Priority is claimed to these applications, and they are incorporated herein by reference in their entireties.

FIELD OF THE INVENTION

The present invention relates to the field of implantable medical devices, and in particular to an improved architecture for an external trial stimulator for use with an implantable neurostimulator.

BACKGROUND

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable neurostimulator.

As shown in FIGS. 1A and 1B, an SCS system typically includes an implantable pulse generator (IPG) 100, which includes a biocompatible device case 130 formed of a conductive material such as titanium. The case 130 typically holds the circuitry and battery necessary for the IPG 100 to function, although IPGs can also be powered via external RF energy and without a battery. The IPG 100 includes one or more electrode arrays (two such arrays 102 and 104 are shown), each containing several electrodes 106. The electrodes 106 are carried on a flexible body 108, which also houses the individual electrode lead wires 112 and 114 coupled to each electrode. In the illustrated embodiment, there are 16 electrodes on array 102, labeled $E_1$-$E_{16}$, and 16 electrodes on array 104, labeled $E_{17}$-$E_{32}$, although the number of arrays and electrodes is application specific and therefore can vary. The arrays 102 and 104 couple to the IPG 100 using lead connectors 138A and 138B, which are fixed in a non-conductive header material, such as an epoxy.

Prior to the implantation of the IPG 100, external trial stimulators are commonly used to insure that the electrodes 106 are properly placed and to allow configuration of the program of stimulation to be performed by the IPG 100. See, e.g., U.S. Patent Publication No. 2010/0228324 (the "'324 Publication"), discussing external trial stimulators in further detail, which is incorporated herein by reference in its entirety. The external trial stimulator connects to electrode lead wires 112 and 114 external to the body of the patient and provides the ability to stimulate the electrodes 106 similar to the way the IPG 100 stimulates once implanted. Current external trial stimulators however can be difficult to manufacture, or have lacked numerous features that would be useful or more comfortable for the patient, physician, or clinical staff.

DETAILED DESCRIPTION

An improved external trial stimulator is disclosed that provides neurostimulation functionality for implanted medical electrodes prior to implantation of an implantable neurostimulator. The external trial stimulator is housed in a four-part housing that provides mechanical and electrostatic discharge protection for the electronics mounted in a central frame of the housing. Connectors attached to leads from the electrodes connect to contacts that are recessed in the housing through ports that are centered for easy access. Multiple indicators provide information to users of the external trial stimulator.

Figure 2:
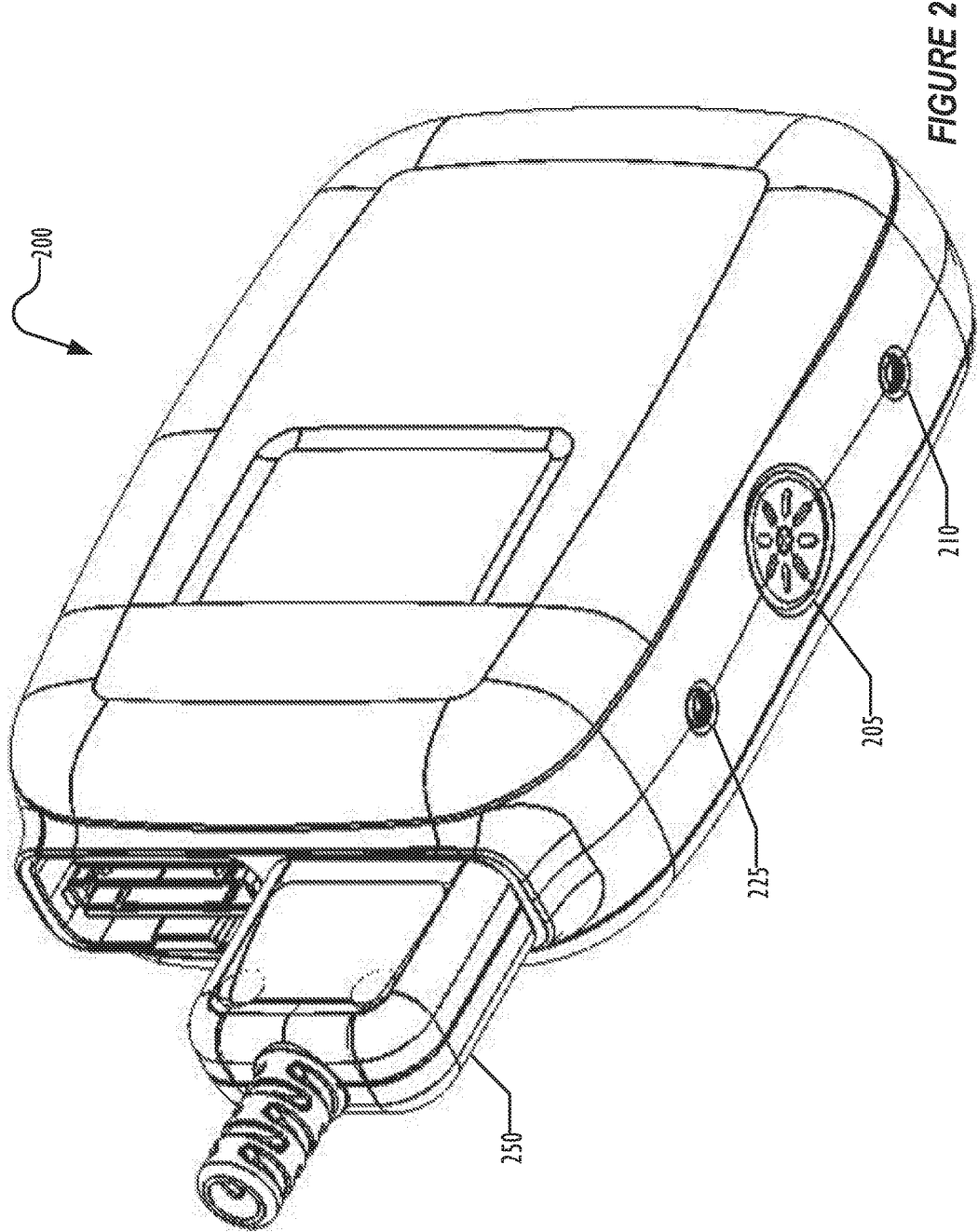
FIG. 2 is a perspective view illustrating an external trial simulator according to one embodiment.

FIG. 2 is a perspective view illustrating an external trial stimulator (ETS) 200 according to one embodiment, with a connector 250 connected to one of the two ports of the ETS 200. A switch 205 allows the patient to turn the ETS 200 on or off. The ETS 200 also provides indicator lights. Indicator light 210 provides information about the charge status of batteries (not shown in FIG. 2) that power the ETS 200. Another indicator light 225 provides information about the status of the ETS 200.

Figure 3:
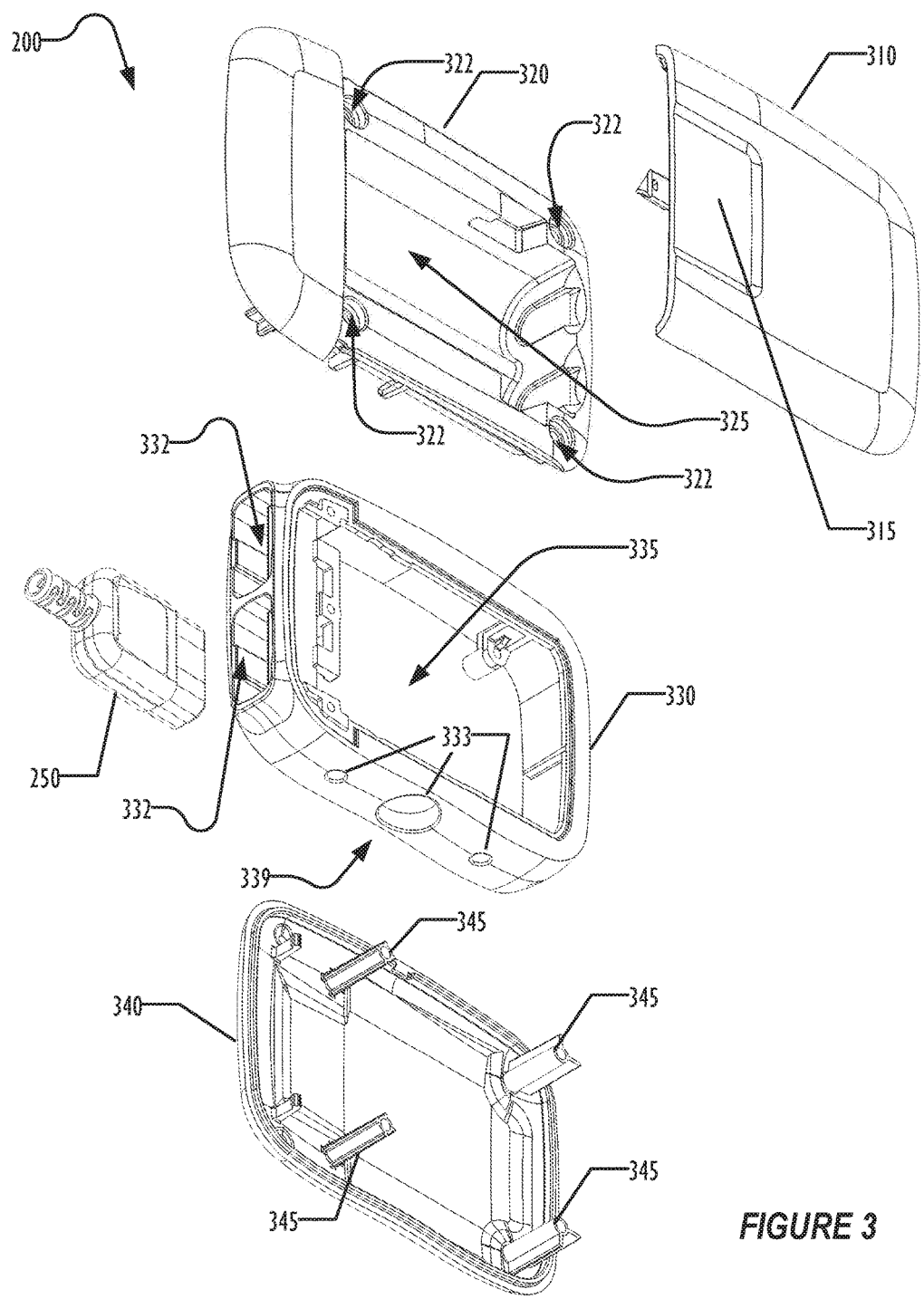
FIG. 3 is an exploded perspective view of the external trial simulator of FIG. 2.

FIG. 3 is an exploded perspective view illustrating various elements of the ETS 200 according to one embodiment. As illustrated in this view, the ETS 200 comprises a four-part housing: a battery cover 310, a top cover 320, a center frame 330, and a bottom cover 340. The top cover 320, center frame 330, and bottom cover 340 are assembled together, typically with screws threaded through screw holes 322 in the top cover 320 into posts 345 of bottom cover 340. The battery cover 310 is removably attached to the top cover 320 using a catch of any type known in the art to allow a patient pressing on indentation 315 to slide the battery cover 310 outwards to remove the battery cover 310 from the top cover 320, gaining access to battery compartment 325 formed in the center of top cover 320. The center frame 330 forms a cavity 335 in which electronics (not shown in FIG. 3) can be attached, protecting the electronics from damage.

Figure 1:
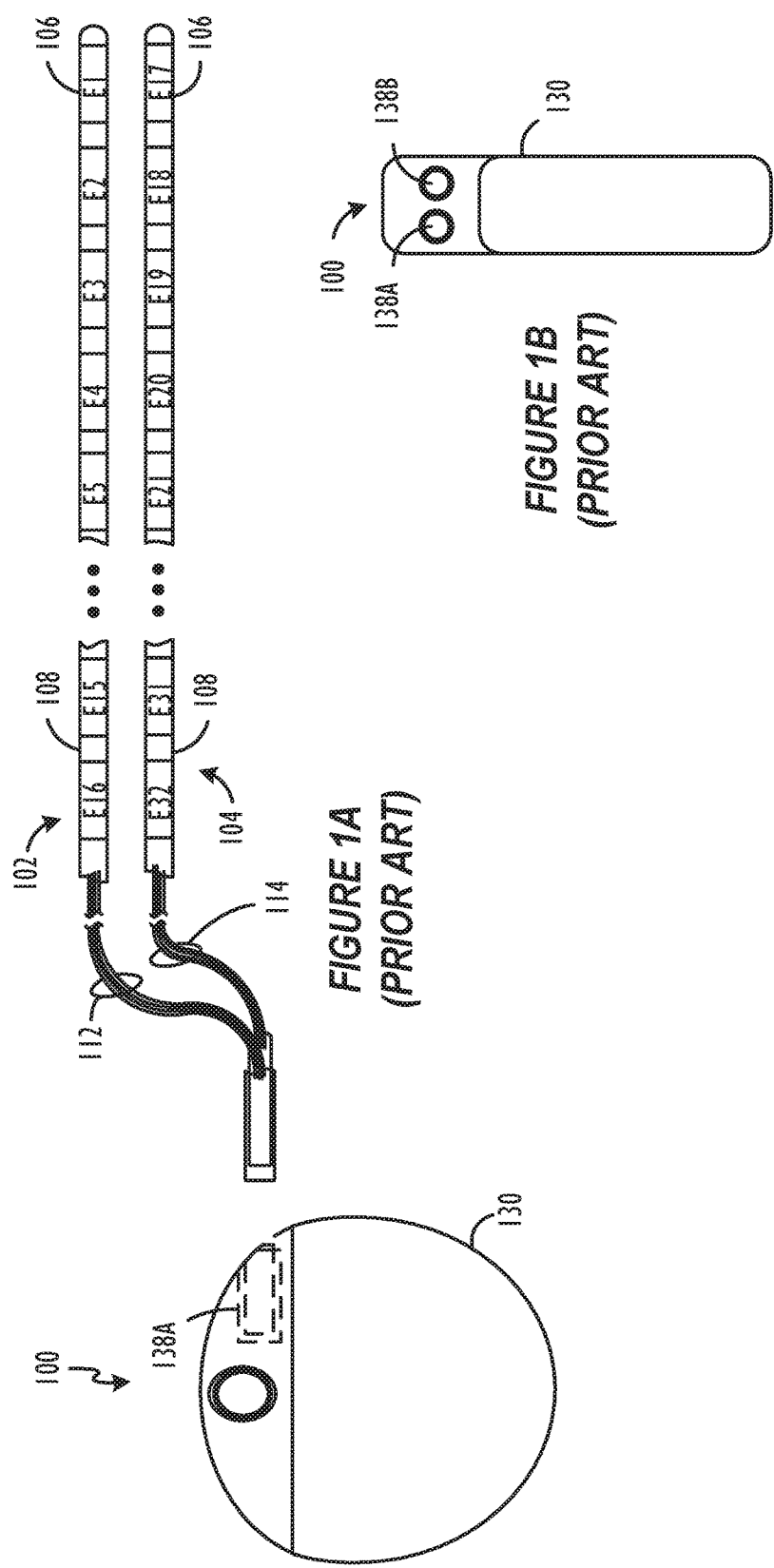
FIGS. 1A and 1B are block diagrams illustrating an implantable medical device according to the prior art.

The center frame 330 also provides two ports 332 for connecting to two connectors 250 (only one of which is shown in FIG. 3). Although not shown, but as explained in the above-incorporated '324 Publication, connectors 250 are coupled to cables that terminate at cable boxes. The ends of the electrode lead wires 112 or 114 (FIG. 1A), or their extensions, can be placed into these cable boxes to ultimately electrically connect each of the electrodes 106 to a corresponding terminal in each of the ports 332. As shown, two connectors 250/ports 332 are used—one for each of the electrode arrays 102 and 104 (FIG. 1A), but other numbers of connectors 250 and ports 332 may be used.

The center frame 330 provides openings 333 for viewing indicators 210 and 225, as well as for accessing switch 205. As illustrated in FIG. 3, in one embodiment, the opening for switch 205 is located at a slightly recessed area 339 of center frame 330, to reduce inadvertent actuation of the switch 205. In one embodiment, the switch 205 is shaped like the recessed area 339 to reduce the likelihood of accidental actuation further. In a further embodiment, the switch 205 provides tactile feedback to let the patient know that the switch 205 has been actuated. The switch 205 is preferably large enough for easy actuation by the patient, and is positioned on the side of the ETS 200 to allow visibility and easy access to the switch 205 when the ETS 200 is worn by the patient (see, e.g., FIG. 10). Other openings 333 in center frame 330, top cover 320, bottom cover 340, or battery cover 310 may be included as desired for viewing or accessing other features of the ETS 200.

The four component mechanical housing illustrated in FIG. 3 provides mechanical robustness for the ETS 200. The top and bottom covers 320 and 340, together with battery cover 310, provide the ability to deform slightly under shock, such as may occur should the patient drop the ETS 200, while the rigid center frame 330 protects the electronics of the ETS 200. The ETS 200 housing is easy to assemble, and in one embodiment can be (excluding the battery cover 310) assembled using a Z-axis stacking of the pieces. In addition, by allowing access to the electronics from either side of the center frame 330, the ETS 200 may be completely tested before enclosing the ETS 200 with the top and bottom covers 320 and 340. In one embodiment, the ports 332 are centered on one end of the center frame 330, allowing easy access regardless of whether the ETS 200 is worn on the right or left side of the patient's body.

In one embodiment, the body parts 310, 320, 330, and 340 are manufactured from a high flow polycarbonate plastic, which provides good impact resistance and structural stability. The center frame 330 may be given a surface finish of a different color or finish than the covers 310, 320, and 340, which may comprise a scratch resistant hard coating.

As illustrated in FIG. 3, the screw holes 322 for use in connecting the components of the ETS 200 may be recessed within the top cover 320 and covered by the battery cover 310 when it is mated with the top cover 320. This ensures that the screws (not shown) are not exposed on the outside of the ETS 200, which reduces the possibility that the screws can promote an electrostatic discharge (ESD) event that might damage the electronics within the ETS 200. Additionally, not having exposed screws eliminates the screws as a possible source of contamination.

Figure 4:
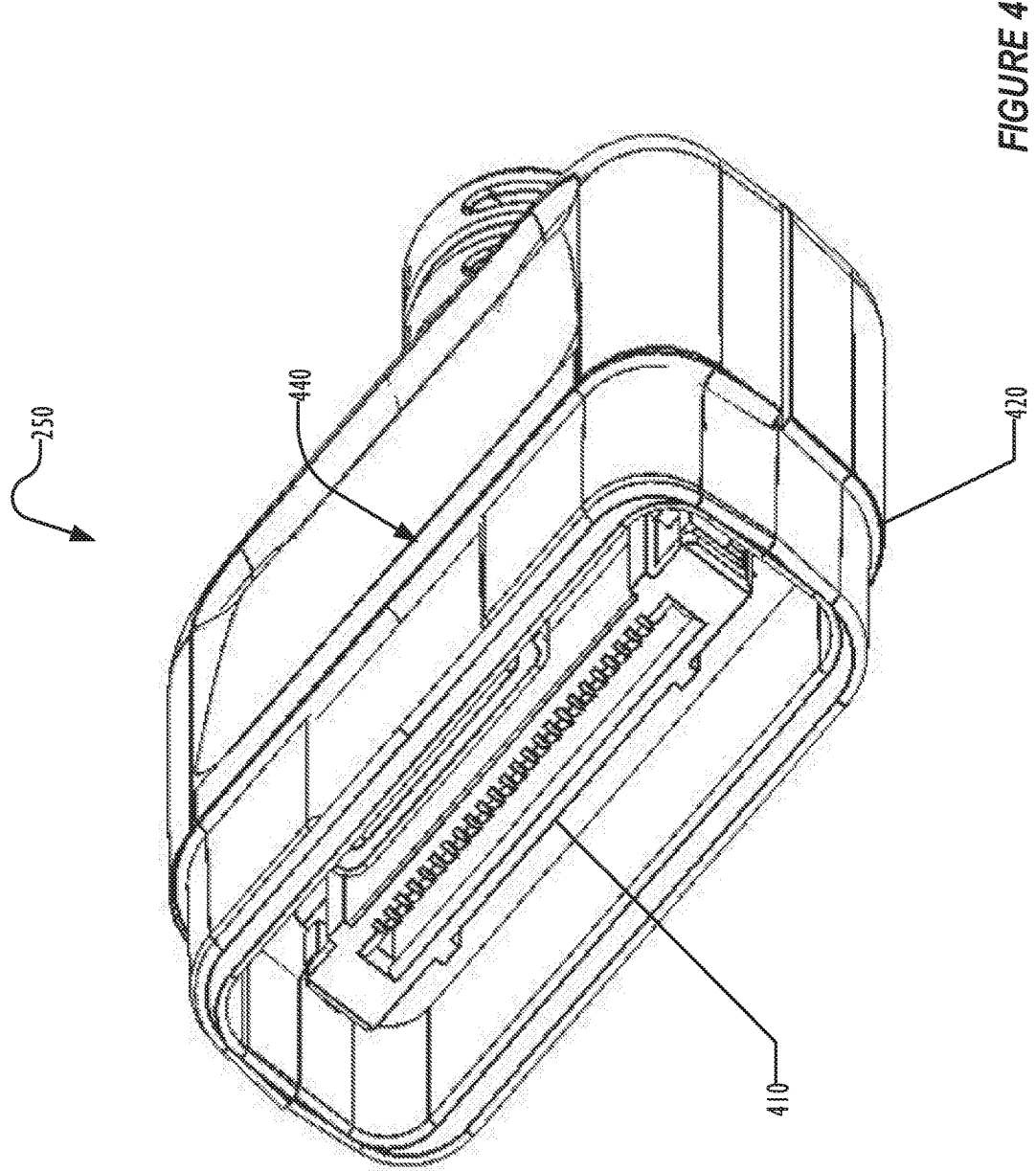
FIG. 4 is a perspective view of a cable connector for use with an external trial stimulator according to one embodiment.

FIG. 4 is a perspective view of a connector 250 according to one embodiment, illustrating electrical contacts 410 formed in a connector housing 420. In one embodiment, an indentation 440 in the connector housing 420 provides an improved gripping area to allow gripping the connector 250 with sufficient force to allow the removal of the connector 250 from the ports 332 of the ETS 200 when desired. In one embodiment, there are 24 high-density electrical contacts 410, and 17 of these contacts 410 are coupled to 17 electrodes—16 of which are electrodes 106 on one of the electrodes arrays 102 or 104 (FIG. 1A), and one of which comprises the IPG's conductive case 130. Other of the remaining 24 contacts can be used to determine lead disconnection, lead addressing, or are simply not used.

As illustrated in FIG. 4, the contacts 410 on the connector 250 are recessed within the connector housing 420 to reduce the likelihood that the contacts 410 may be touched by fingers or other small objects. The contacts 410 in one embodiment employ leaf contacts that latch in place, yet can be easily removed without the need for pushbuttons or other unlatching mechanisms. Use of unlatching mechanisms that require manual disengagement of a latch is less preferred, as it is desired for patient safety that the connector 250 automatically disengages from the ports 332 on the ETS 200 upon exertion of a significant force. Allowing quick disconnection of the connector 250 from the ETS 200 also helps prevent damage to the connector 250 or the ETS 200. At the same time, however, the connector 250 is preferably designed to prevent disconnection from the ETS 200 under normal usage. The indentation 440 allows easier gripping of the connector 250 with sufficient force to disengage it from the ETS 200 when desired. Preferably, the contacts 410 provide a stable mating force between the connector 250 and ports 332 on the ETS 200 that does not depend on pin interference.

In one embodiment, the connectors 250 and the ports 332 are configured to mate only in one orientation, preferably with connectors 250 and ports 332 having shapes that make the correct orientation easily detectable by the patient. This prevents inadvertent connection of the electrodes 106, which could lead to incorrect stimulation by the ETS 200 and possibly danger to the patient.

Figure 5:
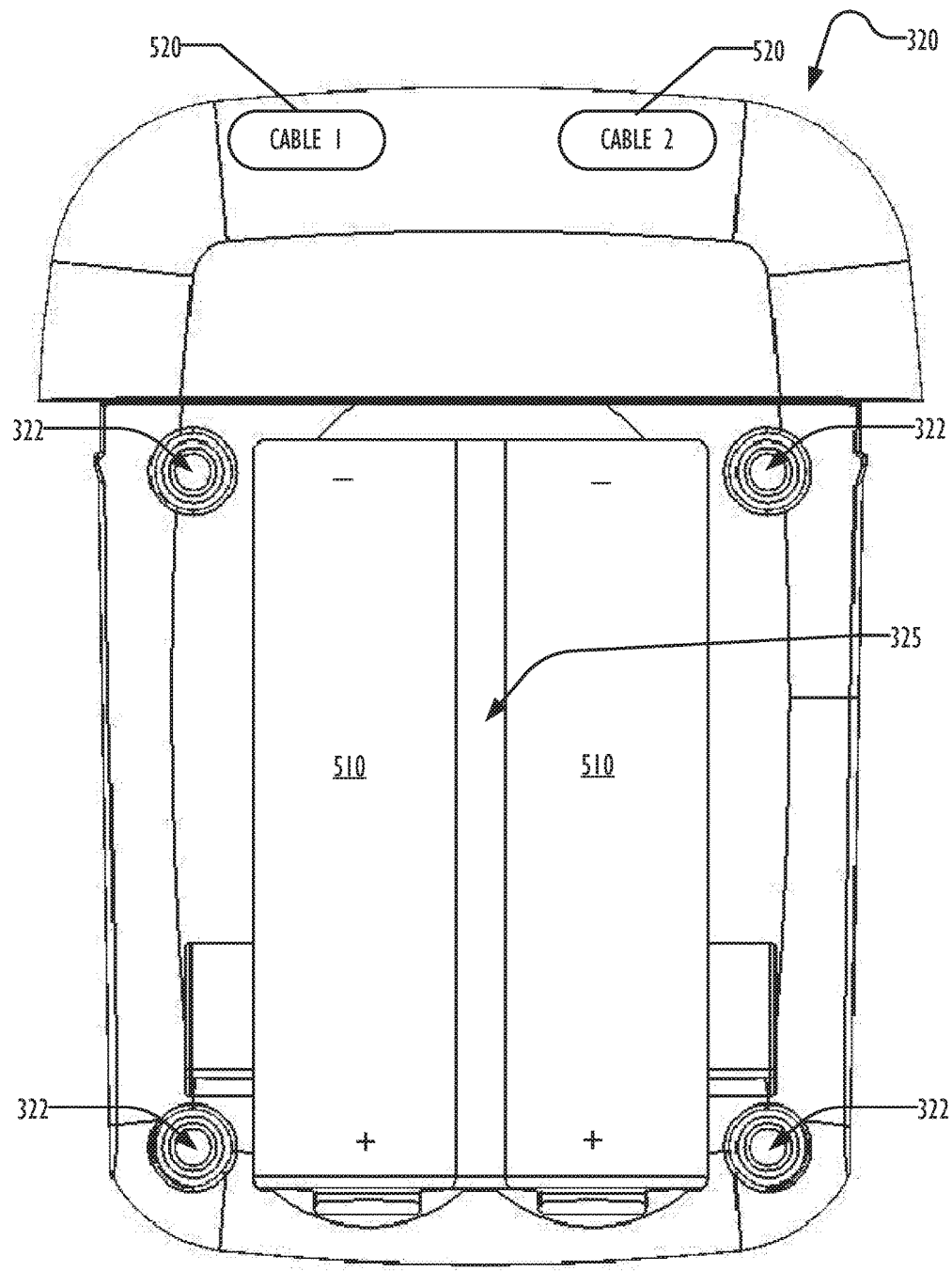
FIG. 5 is a top view of a battery compartment of an external trial stimulator according to one embodiment.

FIG. 5 is a top view of the top cover 320, illustrating placement of batteries 510 in the battery compartment 325. Although as illustrated in FIG. 5 each battery 510 is oriented in the same direction, other embodiments may allow for batteries oriented in different directions. Although two batteries are illustrated in FIG. 5, any number of batteries may be used as desired. As is common in battery-operated devices, the correct orientation of the batteries 510 may be marked on the top cover 320. Similarly, markings 520 may be made on the top cover to assist the connection of connectors 250 to the correct ports 332.

In one embodiment, the batteries 510 are common AA-size batteries, although other types of batteries may be used. In one embodiment, a power converter 820 (FIG. 8) steps up the voltage produced by the AA batteries 510 to a voltage commonly output by Li-ion batteries (e.g., 4.1V). This occurs because the ETS 200 emulates stimulation circuitry residing within the IPG 100, which circuitry is typically powered by a Li-ion battery. In fact, the circuitry internal to the ETS 200 may be the same as the circuitry within the IPG 100, at least to some extent. Using the same circuitry for the ETS 200 and IPG 100 is efficient to design and manufacture.

The battery compartment 325 is configured in one embodiment so the placement of one or both of the batteries 510 in the wrong orientation will prevent the misoriented battery from making electrical contact with the battery terminals, avoiding electrically damaging the ETS 200 circuitry. In another embodiment, techniques for allowing insertion of the batteries 510 in any orientation may be used, although this adds to the manufacturing cost and weight of the ETS 200. In one embodiment, battery misorientation protection involves both mechanical and electrical protection techniques.

Figure 6:
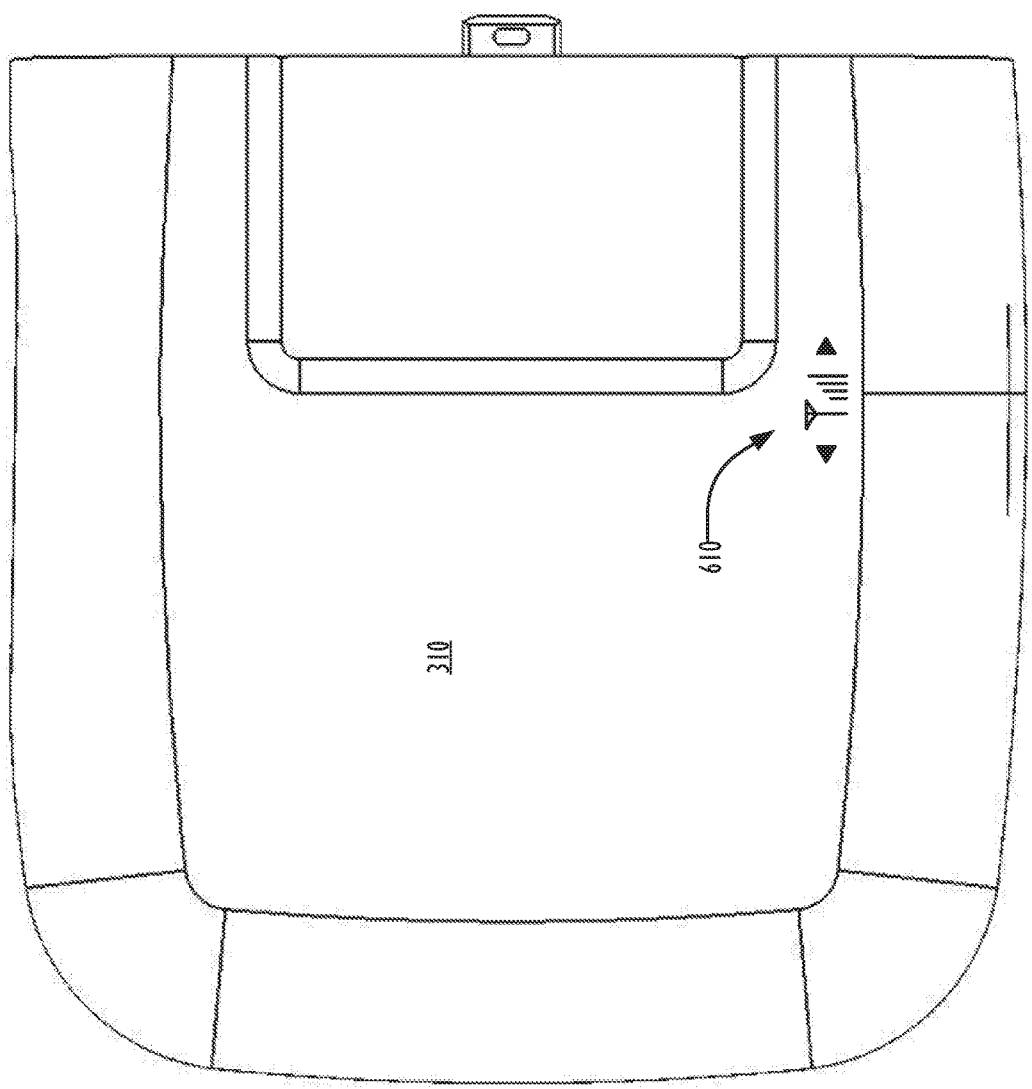
FIG. 6 is a top view of a portion of a housing of an external trial stimulator according to one embodiment.
Figure 7:
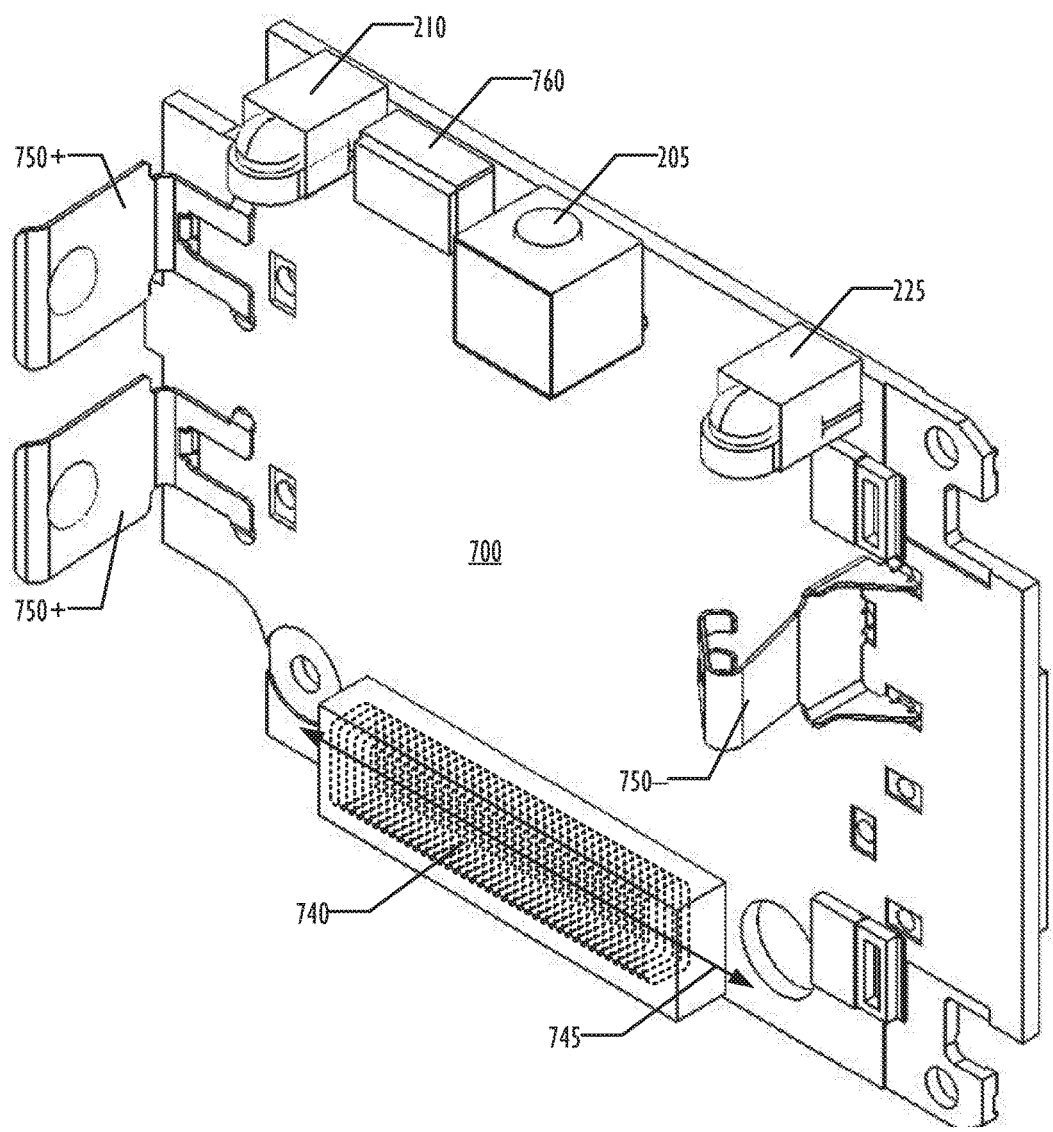
FIG. 7 is a perspective view of one side of a circuit board for an external trial stimulator according to one embodiment.

FIG. 6 is a top view illustrating a battery cover 310 according to one embodiment. As is common in implantable medical device systems, the ETS 200 (like the IPG 100 it emulates) uses telemetry to communicate with an external controller (not shown in FIG. 6), and therefore includes a telemetry antenna 740 (FIG. 7). In one embodiment, an orientation 610 is marked on the battery cover 310 to assist the patient in orienting the external controller relative to the ETS 200 for best communication reliability, which is described in further detail below. As shown in FIG. 6, the external controller is best positioned to the right or left of the ETS 200, although this depends on the orientation of the antenna 740 inside the ETS 200, which can be changed.

Figure 8:
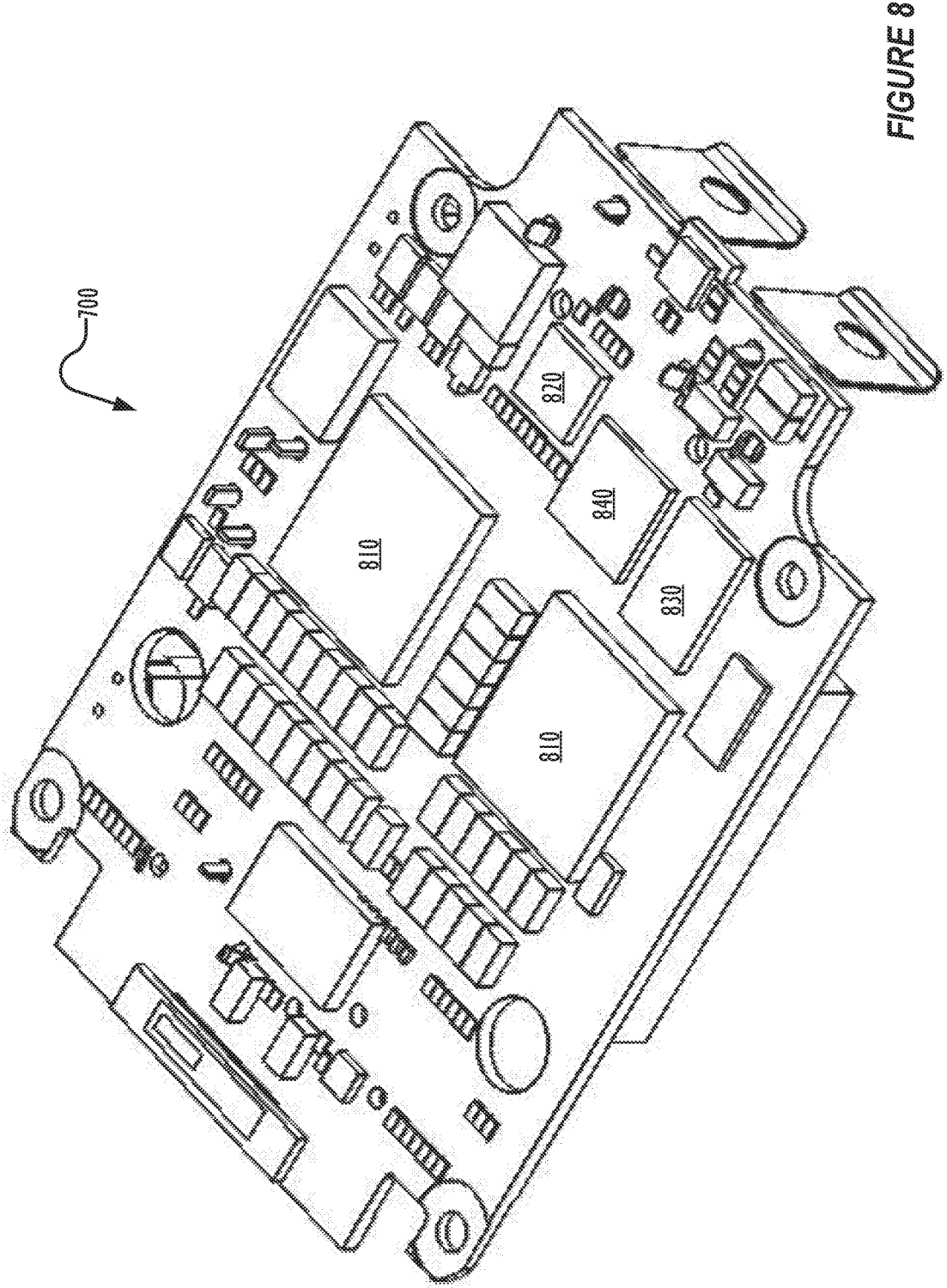
FIG. 8 is a perspective view of the other side of the circuit board of FIG. 7.
Figure 9:
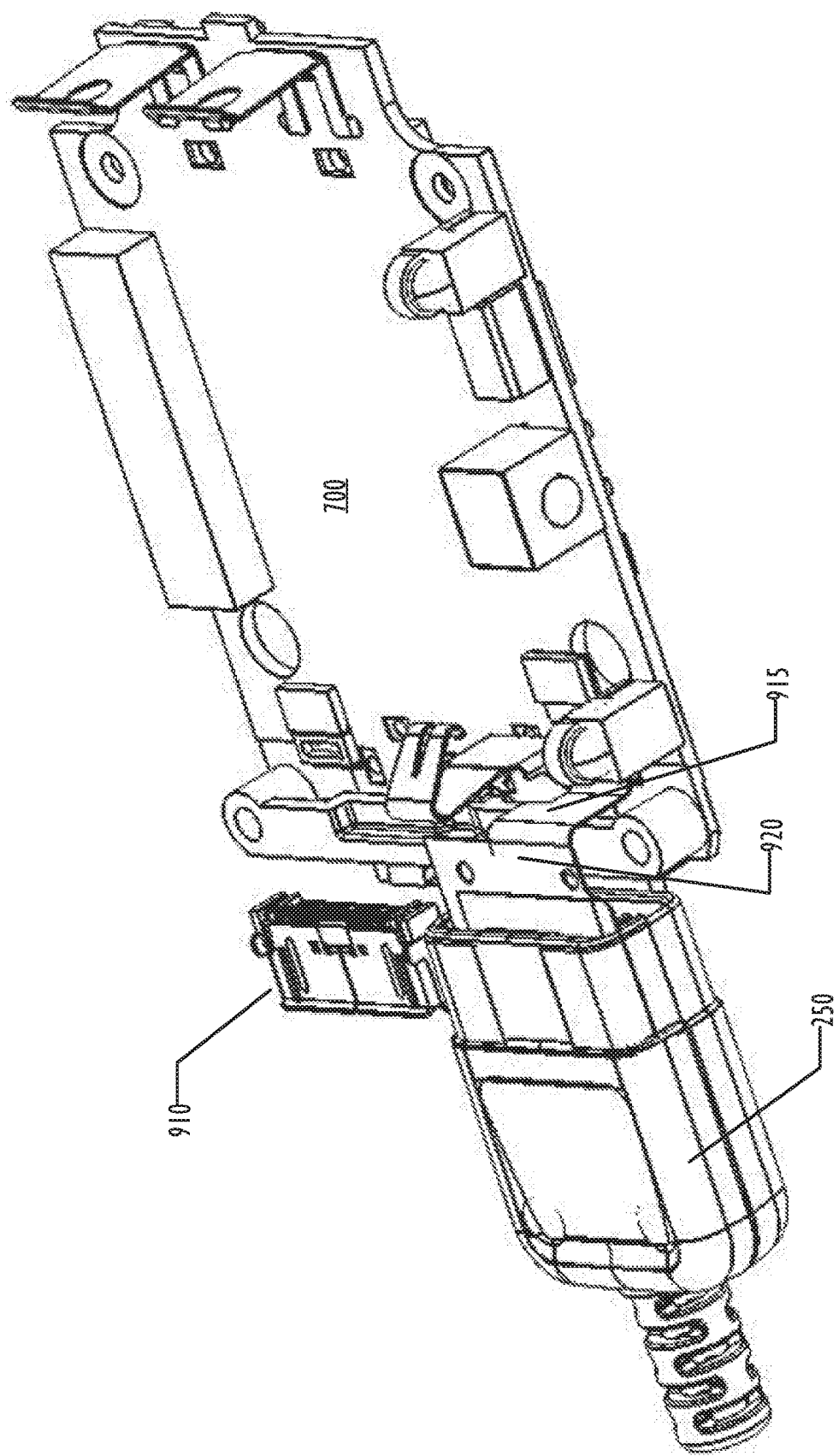
FIG. 9 is a perspective view illustrating connecting a connector to the circuit board of FIG. 7.

FIG. 7 and FIG. 8 are perspective views of a top and bottom side of a first circuit board 700 carrying the electronic components of the ETS 200 according to one embodiment. FIG. 7 illustrates the side proximal to the batteries 510, and includes positive and negative battery terminals 750. Only one negative terminal 750 is illustrated in FIG. 7 for clarity and to show pads for electrically connecting the terminals 750 to the first circuit board 700. The battery terminals 750 in one embodiment may be fully self-supporting on the first circuit board 700, without reliance on mechanical support by the top cover 320 or the central frame 330. (Ports 332 are not shown in FIG. 7 or 8, but are shown in FIG. 9).

In addition to the battery terminals 750, FIG. 7 illustrates indicator lights 210 and 225, switch 205, telemetry antenna 740, and one or more capacitors 760. In one embodiment, indicator lights 210 and 225 are light emitting diodes (LEDs) with a green and yellow LED contained in a housing, allowing the indicator to appear green or yellow to convey information. The LED 210 in one embodiment illuminates green if the battery charge level is sufficient for proper operation of the ETS 200, and yellow when the battery charge level is low.

In one embodiment, LEDs 210 and 225 are driven by an H-bridge and a charge pump to allow use of high-efficiency LEDs with a low current draw. Further power savings may be achieved by blinking the LEDs 210 and 225 at a predetermined rate instead of a constant load. In one embodiment, when power is supplied to the LEDs 210 and 225, the power is gradually ramped up and down, rather than supplied at full power and turned off, to help patients see whether the LED 210 or 225 is turning on or off. This ramped on and off gives the LEDs 210 and 225 an appearance of "breathing," rather than "blinking." Markings (not shown) may be provided on the surface of the center frame 330 proximal to the LED indicators 210 and 225 to help the patient understand the meaning of the LED indicators 210 and 225.

The ETS telemetry antenna 740 comprises a coil, as shown in dotted lines in FIG. 7. Communications between the ETS 200 and an external controller may occur using magnetic induction, and data may be transmitted using a communication protocol such as Frequency Shift Keying (FSK), as is well known in the implantable medical device system arts. Coupling to the external controller will be improved if the external controller is oriented along the axis 745 around which the coil 740 is wound. As discussed earlier with reference to FIG. 6, such optimal orientation 610 for the external controller can be indicated on the battery cover 310, or elsewhere on the ETS's housing. Inductors used on the first circuit board 700 are positioned orthogonal to the axis 745 of the coil 740 to reduce interference with telemetry. The ETS 200 may perform telemetry with external controller to program the ASICs 810 and to report data to the external controller.

In one embodiment, one or more large capacitors 760 are provided on the first circuit board 700 to provide charge storage for temporarily powering the ETS 200 for an orderly shutdown of the ETS 200 when the batteries 510 are removed. These capacitors 760 in one embodiment may be 680 µF tantalum capacitors. The use of the capacitors 760 provides power to avoid corruption of data during a read from or write to the ETS 200, should the batteries be removed during the process of reading or writing.

On the reverse side of the first circuit board 700, as illustrated in FIG. 8, are a number of electronic circuit components that provide functionality for the ETS 200. These components include two application specific integrated circuits (ASICs) 810, each of which handles electrodes 106 coupled to a given one of the connectors 250. The ASICs 810 include programmable neurostimulation logic to generate neurostimulation pulses to the electrodes 106 through lead wires 112 and 114 that are connected to ports 332 via the connectors 250. Also illustrated in FIG. 8 are a power converter 820, a memory 830, and a microcontroller 840. The memory 830 provides storage for software or firmware for the microcontroller 840 and the ASICs 810, as well as for data. The power converter 820 in one embodiment can operate in a high-efficiency power-saving mode that cycles power levels to reduce battery drain and a quiet mode that disables the power cycling. Because the power cycling of the high-efficiency mode may generate magnetic noise that could interfere with telemetry between the ETS 200 and an external device, in one embodiment the power converter 820 may be switched from the high-efficiency mode to the quiet mode for the duration of telemetry activities, then returned to the high-efficiency mode when telemetry is complete.

In one embodiment, before writing to the memory 830, the ETS 200 checks the battery charge status to make sure sufficient charge exists in the batteries 510 to perform the write. If any of the batteries 510 are removed or lose charge during a write, the capacitor 760 provides sufficient backup power to make it more likely to complete the write, reducing the likelihood of data loss or corruption.

FIG. 9 illustrates the first circuit board of 700, with a connector 250 attached. The contacts 410 (FIG. 4) of each connector 250 mate with contacts in a shielded housing 910 positioned in one of the ports 332. The housing 910 contains a second circuit board 920 which is relative rigid and is solderable to the housing contacts in the port 332. The second circuit board 920 is then coupled to first circuit board 700 via a flexible member 915, such as a flexible ribbon cable, to isolate mechanical forces exerted by the connector 250 from the first circuit board 700. The housing 910 may be recessed in the ports 332 of the central frame 330 to provide additional mechanical robustness, such as protection from a drop of the ETS 200.

In one embodiment, the second circuit board 920 is comprised of a laminate composite. Electrical contacts are formed on one end of the second circuit board 920 for mating with the contacts 410 of the connectors 250. A mechanical retention tab and double-sided adhesive tape may be used to anchor the contacts end of second circuit board 920 in place within the port 332 of the ETS 200.

In one embodiment, the ETS 200 may use some of the unused contacts for lead identification, as is discussed in the above-incorporated '324 Publication. As was already discussed with reference to FIG. 5, the ETS 200 may provide markings 520 on the cover 320 to show which of a pair of connectors 250 should be attached through which port 332 of the ETS 200, but patients may still inadvertently insert leads in the wrong port 332, leading to incorrect and possibly dangerous stimulation of electrodes. By providing lead identification, the ETS 200 may detect a connector 250 attached to the wrong port 332 and either automatically redirect signaling to the correct port 332 or indicate a lead misconnection and disable stimulation of electrodes until the misconnection is corrected. All signals output to the ports 332 may be AC coupled, to prevent any chance of delivering DC current to the patient.

In one embodiment, ESD protection may be provided in multiple ways. Each electrode 106 may have individual ESD protection provided by the ASICs 810. In one embodiment, additional ESD protection may be provided by a guard ring around the first circuit board 700. In a further embodiment, the guard ring is discontinuous, to reduce interference. The battery contacts 750 may also have ESD protection.

Figure 10:
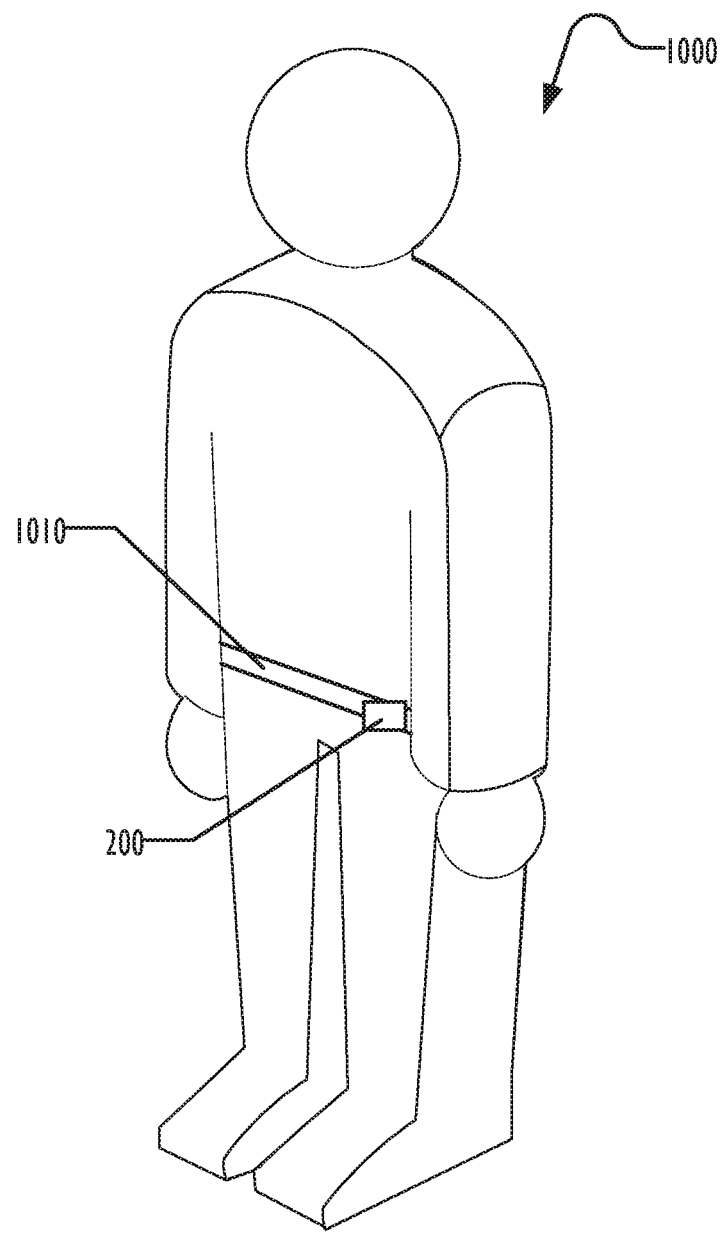
FIG. 10 is a block diagram illustrating a use of an external trial stimulator according to one embodiment.

As illustrated in FIG. 10, ETS 200 is typically worn on a belt 1010, although any other desired method of attaching the ETS 200 to a patient 1000 may be used. The ETS 200 is typically worn with the switch 205 and indicators 210 and 225 pointing upward, where the user can best see and access them.

It is to be understood that the above description is intended to be illustrative, and not restrictive. For example, the above-described embodiments may be used in combination with each other. Many other embodiments will be apparent to those of skill in the art upon reviewing the above description. The scope of the invention therefore should be determined with reference to the appended claims, along with the full scope of equivalents to which such claims are entitled.

What is claimed is:

1. A method of assembling an external trial stimulator, comprising:
    disposing a first circuit board in a cavity of a central housing frame;
    connecting one or more second circuit boards to the first circuit board so that mechanical stress on the one or more second circuit boards is isolated from the first circuit board;
    connecting each of the one or more second circuit boards to a corresponding shielded housing, wherein contacts in each shielded housing are soldered to contacts on the connected second circuit board;
    positioning each shielded housing within a port of the central housing frame; and
    connecting the central housing frame between a first housing cover and a second housing cover.

2. The method of claim 1, further comprising closing a battery compartment in the first housing cover with a battery cover.

3. The method of claim 1, wherein the act of connecting the central housing frame between a first housing cover and a second housing cover comprises screwing the first housing cover, the central housing frame, and the second housing cover together.

4. The method of claim 1, wherein each shielded housing is recessed into the port of the central housing frame within which it is positioned.

5. The method of claim 1, wherein the act of connecting the one or more second circuit boards to the first circuit board comprises connecting each of the one or more second circuit boards to the first circuit board using a flexible member.

6. The method of claim 5, wherein the flexible member is a ribbon cable.

7. The method of claim 1, wherein the contacts in each shielded housing are configured to mate with contacts on a connector that is inserted into the port within which the shielded housing is positioned.

8. The method of claim 1, wherein each port has a shape that accommodates insertion of a connector in only one orientation.

9. The method of claim 1, wherein the central housing frame comprises an opening for accessing a switch that is coupled to the first circuit board.

10. An external trial stimulator, comprising:
    a central housing frame that forms a cavity within which a first circuit board is positioned, the central housing frame comprising one or more ports;
    one or more shielded housings, wherein each shielded housing is positioned within one of the one or more ports and contains a second circuit board, wherein each second circuit board comprises a plurality of contacts that are soldered to contacts on the shielded housing that contains the second circuit board, and wherein each second circuit board is connected to the first circuit board so that mechanical stress on the second circuit board is isolated from the first circuit board; and
    first and second housing covers, wherein the central housing frame is positioned between the first and second housing covers.

11. The external trial stimulator of claim 10, wherein the first housing cover comprises a battery compartment.

12. The external trial stimulator of claim 11, wherein the first housing cover comprises screw holes that are covered by a battery cover.

13. The external trial stimulator of claim 11, wherein the first circuit board comprises a plurality of battery terminals, each battery terminal configured to be coupled to one or more batteries in the battery compartment.

14. The external trial stimulator of claim 13, wherein the first circuit board further comprises one or more capacitors to provide charge storage for temporarily powering the external trial stimulator if the one or more batteries are removed from the battery compartment.

15. The external trial stimulator of claim 10, wherein the first circuit board comprises a switch and one or more indicator lights.

16. The external trial stimulator of claim 15, wherein the central housing frame comprises one or more openings for viewing the one or more indicator lights and an opening for accessing the switch.

17. The external trial stimulator of claim 10, wherein each second circuit board is connected to the first circuit board using a flexible member.

18. The external trial stimulator of claim 17, wherein the flexible member is a flexible ribbon cable.

* * * * *